US00PP18788P3

(12) United States Plant Patent
Heins

(10) Patent No.: US PP18,788 P3
(45) Date of Patent: May 6, 2008

(54) **VARIETY OF *BEGONIA* PLANT NAMED 'SOLENIA SUPER SOFT PINK'**

(50) Latin Name: ***Begonia elatior* hybrid [*Begonia×heimalis*]**
Varietal Denomination: Solenia Super Soft Pink

(75) Inventor: Christiane Heins, Hann. Münden (DE)

(73) Assignee: Ernst Benary Samenzucht GmbH, Hann. Münden (DE)

( * ) Notice: Subject to any disclaimer, the term of this patent is extended or adjusted under 35 U.S.C. 154(b) by 0 days.

(21) Appl. No.: 11/387,328

(22) Filed: Mar. 23, 2006

(65) Prior Publication Data

US 2007/0226860 P1 Sep. 27, 2007

(51) Int. Cl.
*A01H 5/00* (2006.01)

(52) U.S. Cl. ..... Plt./348

(58) Field of Classification Search ..... Plt./348, Plt./347

See application file for complete search history.

(56) References Cited

U.S. PATENT DOCUMENTS

PP10,965 P * 6/1999 Wagner ..... Plt./348
PP11,068 P * 9/1999 Koppe ..... Plt./348

* cited by examiner

*Primary Examiner*—Kent Bell
*Assistant Examiner*—June Hwu
(74) *Attorney, Agent, or Firm*—The Webb Law Firm

(57) ABSTRACT

A new and distinct *Begonia* plant having long-lasting vibrant pink flowers that exhibits good outdoor and garden performance.

2 Drawing Sheets

Botanical classification: *Begonia elatior* hybrid [*Begonia×hiemalis*].
Varietal denomination: 'Solenia Supper Soft Pink'.

BACKGROUND OF THE INVENTION

The present invention comprises a new and distinct cultivar of *Begonia* plant known by the varietal name 'Solenia Super Soft Pink'. The new variety was discovered in 1998 in a selected breeding program in Gimte, Germany. The purpose of the breeding program was to develop a new variety with high sun and rain resistance, as well as good garden and outdoor performance. The new variety is the result of a cross between STHR 47/412 (female parent, unpatented) and TS 24/124 (male parent, unpatented). The new variety differs in flower color, habit and foliage characteristics from both parents. STHR 47/412 is a typical tuberous *begonia*. The flowers are bigger, ball-shaped and highly double in comparison to the new variety. Further, the leaf is smaller with a slight pubescence. TS 24/124 is a *Begonia Socotrana* with small, oval-shaped single flowers and big, flat and shiny leaves. In comparison to other varieties, 'Solenia Super Soft Pink' has medium-sized, fully double flowers. Also, its leaves are bright green and flat. Compared to *Begonia* 'Solenia Rosa' (U.S. Plant Pat. No. PP10,573), the new variety exhibits leaves having an upper surface color of 139A and a lower surface color of 139C while 'Solenia Rosa' exhibits reddish-toned leaves having an upper surface color of 147A and a lower surface color of 59A. Further, the new variety exhibits a flower color of 61D while 'Solenia Rosa' exhibits a flower color of 47C. The new variety was first asexually reproduced in the winter 1998/1999 season by cuttings in Germany. The new variety has been trial and field tested in Germany and has been found to retain its distinctive characteristics and remain true to type through successive propagations.

The following traits also distinguish 'Solenia Super Soft Pink' as a new and distinct cultivar:

1. The flower color is light pink; and
2. The new variety exhibits good outdoor and garden performance.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
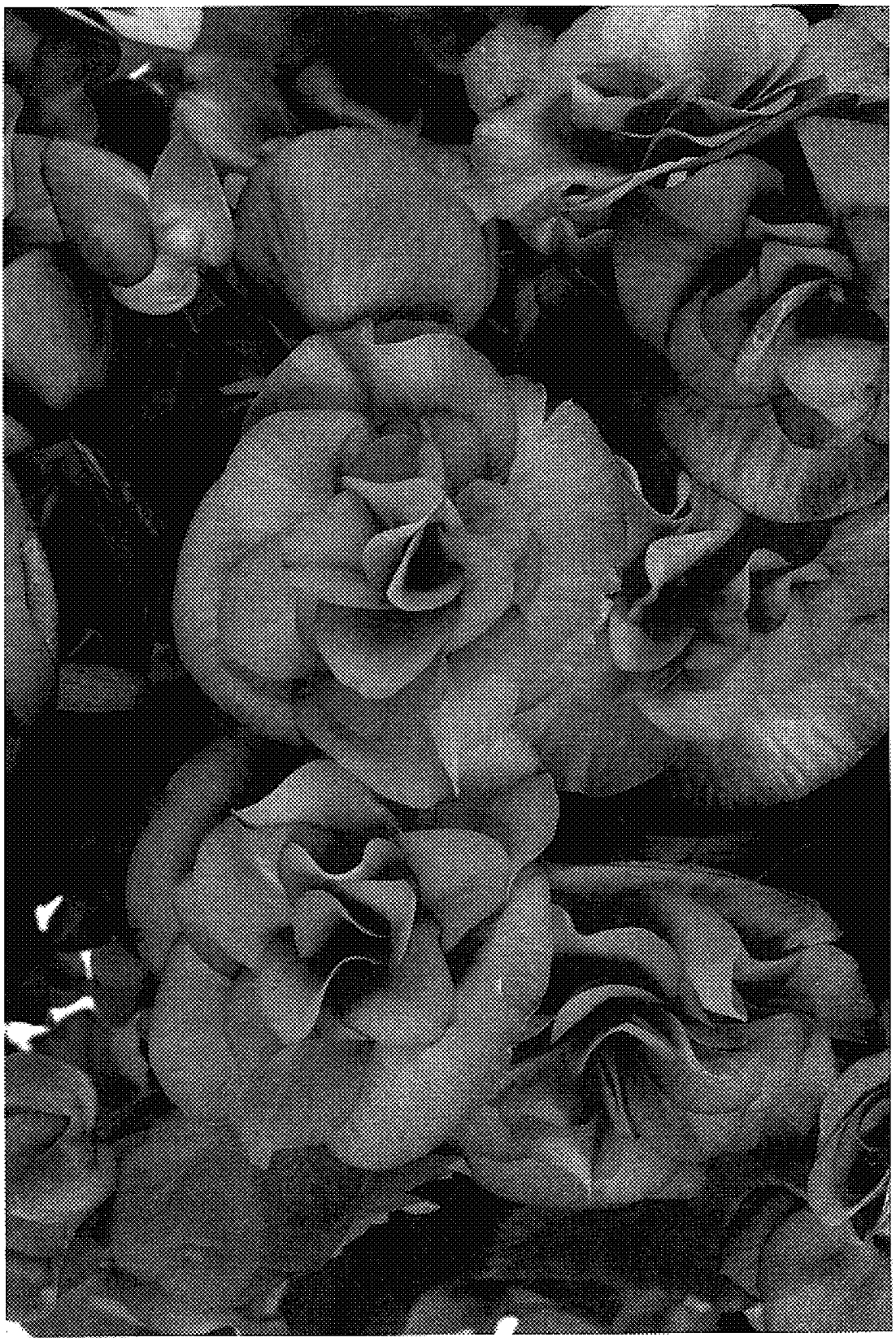
FIG. 1 is a close-up photograph of the flowers of the new variety.
Figure 2:
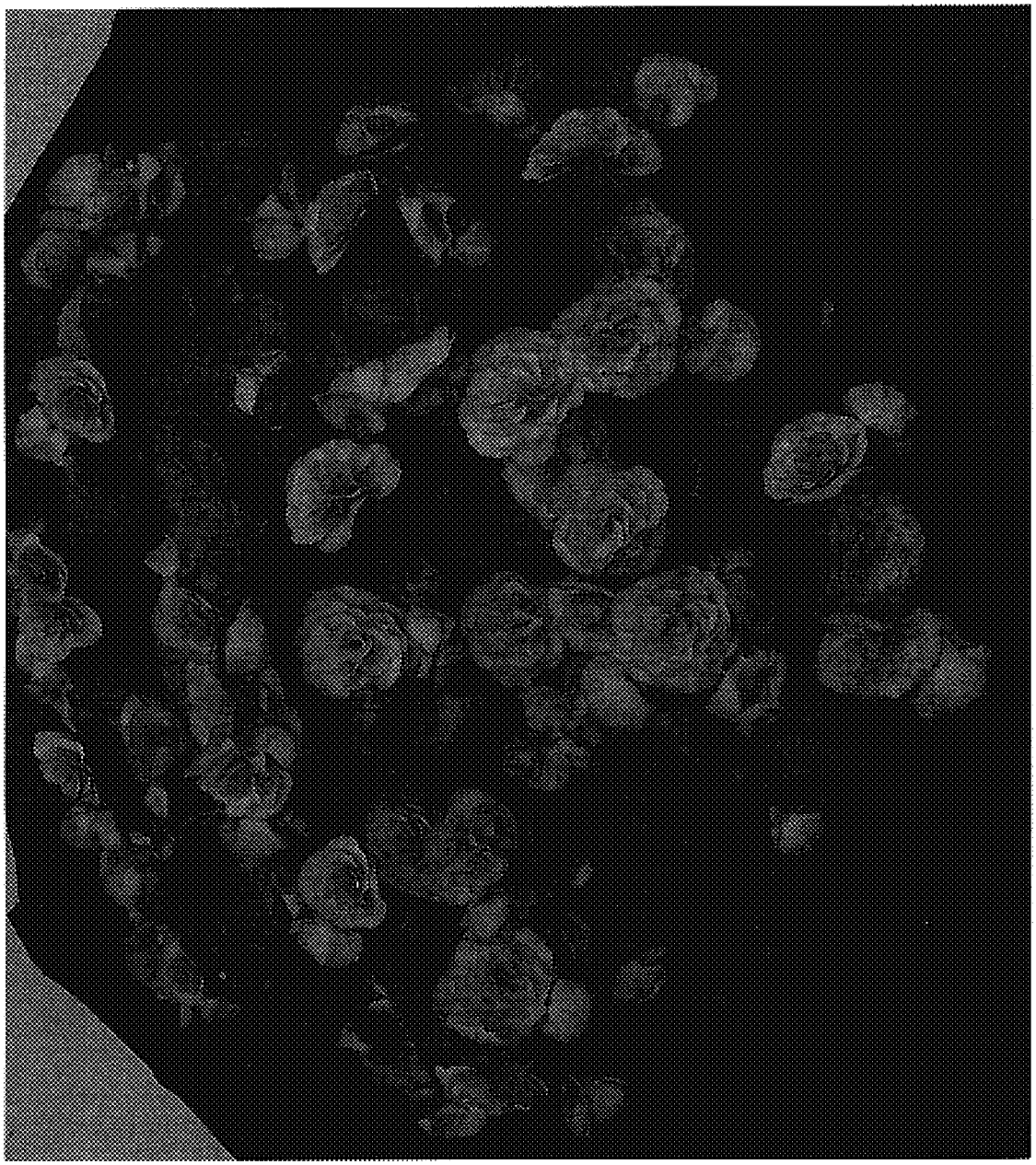
FIG. 2 is photograph of an entire plant of the new variety.

The following detailed description sets forth characteristics of the new cultivar. The data which defines these characteristics were collected by asexual reproductions by cuttings carried out in Germany. The plants were exposed to an average temperature of 18° C. and 14 hours of long day light. Plants for the description were 6 months old and in 13 cm containers. The color readings were taken indoors under natural light. Color references are primarily to the R.H.S. Colour Chart of the Royal Horticultural Society of London.

PLANT

Time to initiate roots: Two weeks at 20° C.
Time to develop roots: Four weeks at 20° C.

Form.: Upright.
Height from soil to top of flowers: 9.84" (25 cm).
Plant diameter: 13.39" (34 cm).
Vigor: Good.
Branching habit: Medium.
Tubers: Not present.
Lateral branches:
*Color.*—144B.
*Texture.*—Smooth.
*Length.*—7.09" (18 cm).
*Diameter.*—6.3" (16 cm).
*Internode length.*—0.98" (2.5 cm).
*Strength.*—A couple of strong branches are exhibited by the new variety.
*Quantity.*—5.
Foliage:
*Arrangement.*—Alternate.
*Number of leaves per stem.*—4 to 5.
*Size of leaf.*—Length: 5.5" (14 cm). Width: 4.3" (11 cm).
*Shape of leaf.*—Dissymmetrical.
*Shape of apex.*—Acute.
*Shape of base.*—Slightly overlapping.
*Texture.*—Upper surface: Smooth and shiny. Lower surface: Smooth and shiny between venation.
*Margin type.*—Bicrenate.
*Fragrance.*—None present.
*Color.*—Young and mature leaves: Upper surface: Green Group 139A. Lower surface: Green Group 139C.
*Petiole.*—Length: 1.57" (4 cm). Diameter: 0.12" (0.3 cm). Color: Yellow-Green Group 145B. Texture: Very small pubescence present.
*Veins.*—Venation pattern: Fan-shaped. Color: Upper surface: Green Group 137C. Lower surface: Green Group 137D.

FLOWER

Natural flowering season: May/June in Germany.
Flower habit: Multiflora, double flowering.
Number of flowers per plant. 60–80.
Time of day of flower opening: Flowers are always open.
Longevity: 3–4 weeks on the plant.
Flower height: 0.79" (2 cm).
Flower diameter: 2.36" (6 cm).
Bud:
*Stage of development when described.*—At the beginning of opening.
*Shape.*—Semi-circle.
*Diameter.*—1.57" (4 cm).
*Length.*—0.98" (2.5 cm).
*Color.*—Red-Purple Group 61D.
Cyme:
*Height.*— 18 7.8" (~20 cm).
*Diameter.*— ~7.4" (~19 cm).
*Number of flowers per cyme.*—5.
Tepals:
*Arrangement.*—Double.
*Quantity.*—25–30.
*Length.*—1.18" (3 cm).
*Width.*—1.57" (4 cm).
*Shape.*—Semi-circle.
*Apex.*—Round.
*Base.*—Even and straight.
*Margin.*—Entire.
*Texture.*—Slightly grooved.
*Color.*—When opening and fully opened (both surfaces): Red-Purple Group 61D.
*Base color of outer tepals when opening.*—Red-Purple Group 58B.
Bracts:
*Average number per flower.*—2.
*Size.*—3 cm×2 cm.
*Shape.*—Heart-shaped (rounded).
*Color.*—Yellow-Green Group 146A.
Peduncles:
*Length.*—2.76"–3.54" (7–9 cm).
*Diameter.*—0.16" (0.4 cm).
*Color.*—Green Group 143B.
*Texture.*—Smooth.
*Orientation.*—Upright.
*Strength.*—Strong.
Pedicels:
*Length.*—0.39" (1 cm).
*Width.*—0.08" (0.2 cm).
*Color.*—Yellow-Green Group 146B.
*Strength.*—Strong.
*Orientation.*—Angled.
*Surface texture.*—Smooth.
Disease resistance: No unusual susceptibility noticed to date.
Weather tolerance: Tolerant in temperatures from 54–86° F. (12–30° C.).
Stamens: None present.
Style color: Greyed-Orange Group 168D.
Pistils: None present.
Stigma:
*Shape.*—Typical for varieties of this type.
*Color.*—Orange Group 28A.
*Ovary color.*—Light green.
Pollen: None present.
Fruit: None present.

I claim:

1. A new and distinct variety of *Begonia* plant substantially as shown and described.

* * * * *

UNITED STATES PATENT AND TRADEMARK OFFICE

CERTIFICATE OF CORRECTION

PATENT NO. : PP 18,788 P3
APPLICATION NO. : 11/387328
DATED : May 6, 2008
INVENTOR(S) : Heins It is certified that error appears in the above-identified patent and that said Letters Patent is hereby corrected as shown below:

Column 1, line 3, "'Solenia Supper Soft Pink'" should read -- 'Solenia Super Soft Pink' --

Column 4, line 2, "18 7.8" should read -- ~ 7.8" --

Signed and Sealed this

Thirtieth Day of September, 2008

JON W. DUDAS
*Director of the United States Patent and Trademark Office*